(12) United States Patent
Wozencroft (10) Patent No.: US 8,721,593 B2
(45) Date of Patent: May 13, 2014

(54) INJECTION DEVICE

(75) Inventor: Robert Michael Wozencroft, Surrey (GB)

(73) Assignee: Owen Mumford Limited, Oxford (GB)

( * ) Notice: Subject to any disclaimer, the term of this patent is extended or adjusted under 35 U.S.C. 154(b) by 634 days.

(21) Appl. No.: 12/993,955

(22) PCT Filed: May 20, 2009

(86) PCT No.: PCT/GB2009/050542
§ 371 (c)(1),
(2), (4) Date: Nov. 22, 2010

(87) PCT Pub. No.: WO2009/141650
PCT Pub. Date: Nov. 26, 2009

(65) Prior Publication Data
US 2011/0077599 A1    Mar. 31, 2011

Related U.S. Application Data

(60) Provisional application No. 61/071,931, filed on May 27, 2008.

(30) Foreign Application Priority Data

May 20, 2008 (GB) .................................. 0809134.0

(51) Int. Cl.
*A61M 5/00* (2006.01)
*A61M 3/00* (2006.01)

(52) U.S. Cl.
USPC .......................................... 604/111; 604/189

(58) Field of Classification Search
USPC ......... 604/111, 181, 187, 189, 192, 194, 198, 604/207–211, 218, 225, 226, 228, 260; 116/204, 267
See application file for complete search history.

(56) References Cited

U.S. PATENT DOCUMENTS 3,880,163 A    4/1975   Ritterskamp
4,959,056 A *  9/1990   Dombrowski et al. ....... 604/186

(Continued)

FOREIGN PATENT DOCUMENTS

DE    10 2004 052219 A1    5/2006
EP         1 568 393 A1    8/2005

(Continued)

OTHER PUBLICATIONS

International Search Report, dated Dec. 4, 2009, from corresponding PCT application.

(Continued)

*Primary Examiner* — Kevin C Sirmons
*Assistant Examiner* — Andrew Gilbert
(74) *Attorney, Agent, or Firm* — Young & Thompson (57) ABSTRACT

An autoinjector is provided with a magnetically operated "injection complete" indicator. A moveable magnet (44) associated with the drive piston (38) is kept at one end of a recess by a soft iron keeper (46) until the drive piston reaches its formal position where the moveable magnet (44) is attracted to impact a magnet (48) on the housing to generate an audible click. Also described is a spring finger (52) that slips behind the rear edge of the syringe boot (50) temporarily to hold the end of the boot well clear of the housing to that it can be gripped for removal.

19 Claims, 7 Drawing Sheets

(56) References Cited

U.S. PATENT DOCUMENTS

| | | | |
|---|---|---|---|
| 5,628,309 A * | 5/1997 | Brown | 600/310 |
| 6,033,377 A * | 3/2000 | Rasmussen et al. | 604/82 |
| 6,203,530 B1 | 3/2001 | Stewart, Sr. | |
| 6,221,044 B1 | 4/2001 | Greco | |
| 6,221,046 B1 * | 4/2001 | Burroughs et al. | 604/153 |
| 6,319,234 B1 | 11/2001 | Restelli et al. | |
| 2003/0083611 A1 | 5/2003 | Angel et al. | |
| 2004/0210199 A1 * | 10/2004 | Atterbury et al. | 604/224 |
| 2005/0020983 A1 * | 1/2005 | Schreijag et al. | 604/187 |
| 2006/0161112 A1 * | 7/2006 | Steffen | 604/188 |
| 2006/0173409 A1 | 8/2006 | Yang | |
| 2006/0175427 A1 * | 8/2006 | Jonientz et al. | 239/69 |
| 2006/0184133 A1 | 8/2006 | Pessin | |
| 2007/0005021 A1 * | 1/2007 | Kohlbrenner et al. | 604/208 |
| 2007/0173772 A1 | 7/2007 | Liversidge | |
| 2009/0131875 A1 * | 5/2009 | Green | 604/187 |
| 2013/0310745 A1 * | 11/2013 | Latham et al. | 604/131 |

FOREIGN PATENT DOCUMENTS

| | | | | |
|---|---|---|---|---|
| GB | 2 414 398 A | 11/2005 | | |
| WO | 99/22792 A1 | 5/1999 | | |
| WO | 00/24441 A1 | 5/2000 | | |
| WO | 2005/009515 A1 | 2/2005 | | |
| WO | 2005/009519 A1 | 2/2005 | | |
| WO | 2006/134153 A1 | 12/2006 | | |
| WO | 2008/024814 A2 | 2/2008 | | |
| WO | 2008/083875 A1 | 7/2008 | | |
| WO | WO 2008/083875 A1 * | 7/2008 | | A61M 5/315 |

OTHER PUBLICATIONS

British Search Report, dated Jul. 31, 2008, from corresponding British application.

* cited by examiner

INJECTION DEVICE

This invention relates to injection devices, and in particular, but not exclusively, to reusable auto-injector devices comprising a housing into which a disposable syringe may be inserted to effect the injection and then removed and replaced as required for the next injection.

BACKGROUND OF THE INVENTION

It is a requirement that auto-injectors signal to the user when the injection is complete. Most have a visible indication, but sometimes the injection site is out of sight or would require some straining to see, for example in the buttocks or upper arm. It is therefore desirable to have an audible or tactile 'injection complete' signal. The term 'injection complete' is used to refer to a condition in which a satisfactory delivery of the drug has been achieved.

SUMMARY OF THE INVENTION

In one aspect this invention provides an injection device comprising a housing, a syringe disposed within said housing, and a magnetically-operated indicator for generating an injection complete indication. In the described embodiment, the use of a magnetically-operated device means that at least some of the energy required for creating the indication is derived from magnetic attraction (or repulsion) meaning that little or no energy is diverted from the main injection spring.

In another aspect, this invention provides an injection device including:
 a syringe disposed within a housing;
 a drive element moveable from a first position to a second position to expel a dose from said syringe;
 a magnetically operated indicator for indicating injection complete;
 said indicator including two co-acting elements associated one with said drive element and one with said housing respectively, and arranged such that, as said drive element arrives at or near said second position, the relative position of said co-acting elements is changed by the influence of magnetic force acting therebetween.

As above, the injection complete indication is generated magnetically. The indication is generated by the change in position of the two co-acting elements.

Numerous different magnetic configurations are possible. In one arrangement, one of the co-acting elements comprises a captive element and the other comprises a relatively moveable element. Thus said captive element may be associated with the housing and the relatively moveable element may be associated with the drive element. Although not essential, it is preferred for both said co-acting elements to be magnetised.

In a preferred arrangement, the drive element has a ferromagnetic keeper element associated with it adapted temporarily to restrain said moveable magnetic element until it is moved under the influence of magnetic force due to proximity of said captive magnetic element. In this way a light restraining force is applied to the moveable magnetic element until it is close enough to the captive element to be pulled away from the keeper by the magnetic force.

The injection complete indication may take many forms, for example it may comprise one or more of an audible indication, a visual indication or a tactile indication. Where the indicator provides an audible indication, this may be produced as a result of impact between the moveable magnetic element and the captive magnetic element (or a surface associated therewith). In this arrangement the drive element may have associated therewith a recess for receiving the relatively moveable magnetic element and allowing generally transverse movement of the moveable element due to magnetic interaction with the fixed magnetic element. The recess may extend transversely and have at one end thereof the keeper element, with the other end of the recess facing the fixed co-acting element when the drive element is in its second position. The recess may be provided in a drum which forms part of the drive assembly and which is acted upon by a spring.

Whilst in many embodiments the drive element will move linearly to expel a dose from the syringe, the invention extends to arrangements in which the movement of the drive member is non-linear, for example rotary.

In many auto-injector devices, a syringe with a sheath covering its needle is loaded into the device and the sheath has to be removed prior to operation. It is a feature of some existing auto-injector devices that the sheath covering the needle is difficult to remove once the syringe has been inserted into the device because only a very short portion of the sheath protrudes. Due to this problem, the user may decide to remove the sheath prior to inserting the syringe into the auto-injector and this increases the risk of accidental needle-stick injury. For a given length of sheath, if the device is designed so that a greater proportion of the sheath is accessible this would mean that the exposed needle tip would protrude beyond the housing and again this would lead to potential needle-stick injury.

Accordingly, in another aspect of this invention there is provided an injection device comprising:
 a housing having a forward end;
 a syringe having a needle at its forward end and disposed within said housing for longitudinal movement;
 a removable needle sheath covering the needle prior to use;
 the syringe being moveable forwards against a spring bias prior to injection to cause said needle sheath to move to an extended position in which a forward portion of said sheath projects from said housing to allow it to be gripped and removed from the needle, and
 a latch for releasably latching at least one of said syringe and sheath so that said sheath is held in its extended position.

In this arrangement, the syringe may be moved forwardly against a spring bias so that the latch holds the syringe and/or sheath so that sufficient portion of the sheath is exposed to allow it to be gripped and removed.

It is preferred for the sheath to have a rearwardly facing surface and said latch to latch behind said rearwardly facing surface. This means that, on removal of the sheath, the syringe is urged rearwardly by its spring bias to move the needle back from the forward end of the housing. Thus for example, the rearwardly facing surface on the sheath may comprise the generally annular rim at the rear end of the sheath.

The latch may conveniently comprise a forwardly extending resiliently deflectable finger having a latch surface at a forward end region and its rearward end region being secured to said housing.

Whilst the invention has been described above, it extends to any inventive combination of the features set out above or in the following description or claims.

BRIEF DESCRIPTION OF THE DRAWINGS

The invention may be performed in various ways and an embodiment thereof will now be described by way of example only, reference being made to the accompanying drawings in which.

DETAILED DESCRIPTION OF THE PREFERRED EMBODIMENTS

Figure 1:
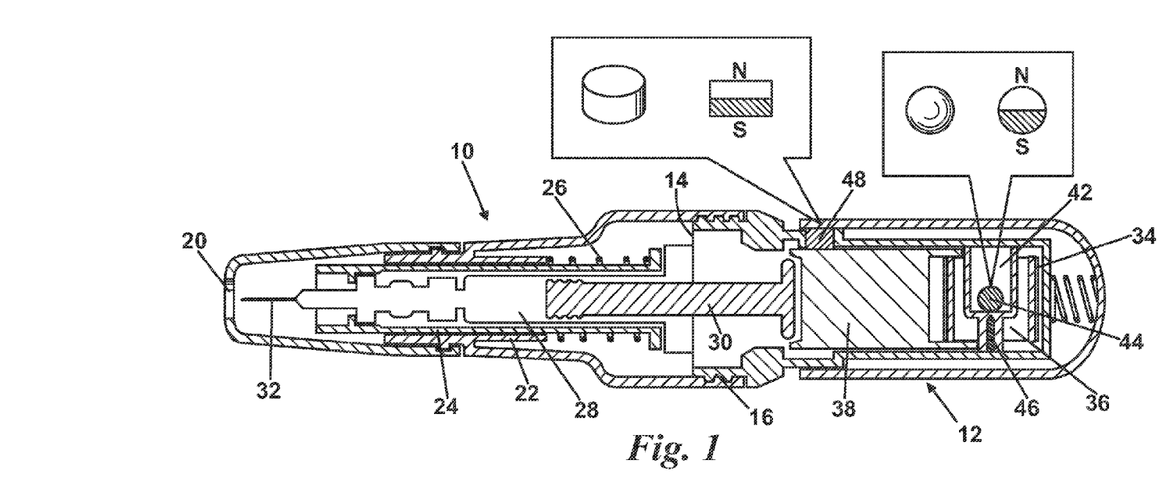
FIG. 1 is a cross-sectional view through an embodiment of the auto-injector in accordance with this invention, with the drive piston in the cocked position.
Figure 2:
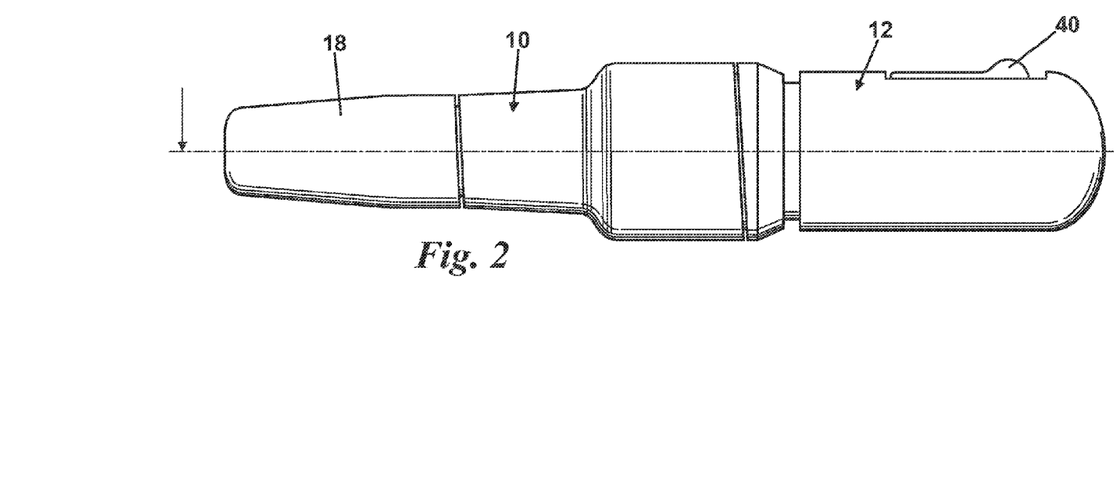
FIG. 2 is a side view of the auto-injector device.
Figure 3:
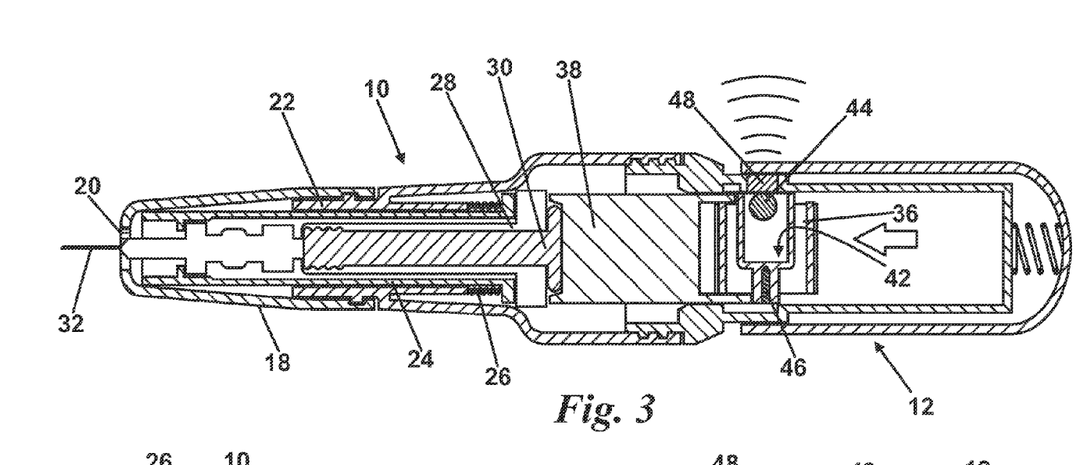
FIG. 3 is a cross-sectional view through the auto-injector of FIGS. 1 and 2 with the syringe extended and the dose expelled and generating an injection complete indication.
Figure 4:
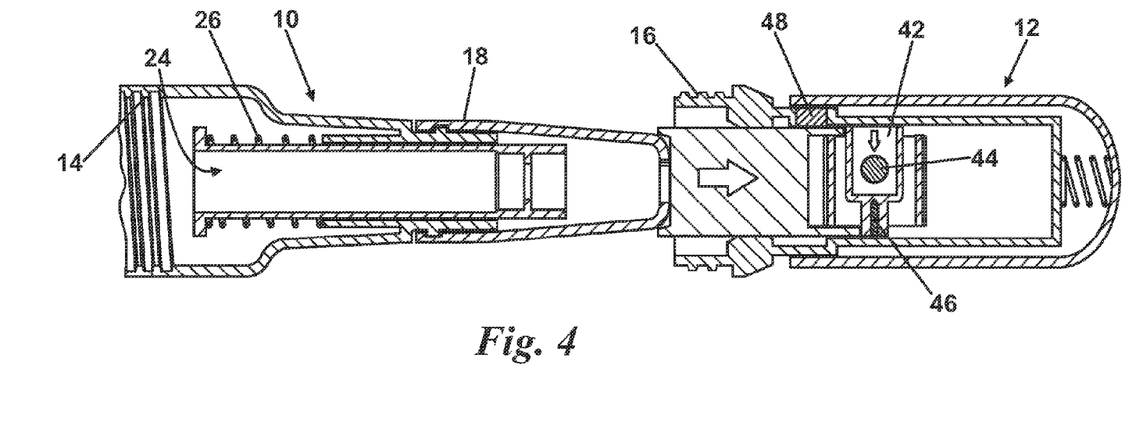
FIG. 4 is a cross-sectional view showing the front end of the auto-injector unscrewed and reversed to cock the drive piston.
Figure 5:
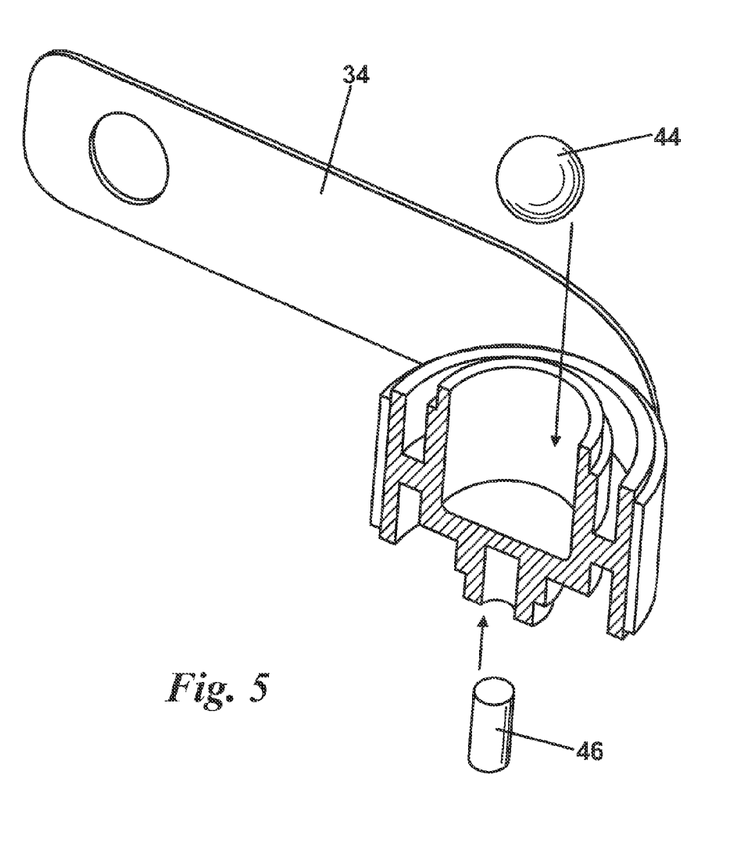
FIG. 5 is a general perspective view showing the spring drum and constant force spring used in the embodiment of FIGS. 1 to 4.

Referring initially to FIGS. 1 to 5, there is shown an auto-injector device comprising a front housing part 10 and a rear housing part 12, having respective screw threaded portions 14, 16 to allow the parts to be screwed together as seen in FIGS. 1 to 3. The front and rear housing parts may be seen clearly in FIG. 4.

The front housing part is provided at its forward end with a captive depth adjustment cap 18 having an aperture 20 at its forward end through which the syringe needle may project. The forward housing part 10 is provided with an internal collar 22 which slideably receives a syringe carrier 24 which is biased rearwardly by a spring 26. The syringe carrier 24 has an internal bore designed to receive a syringe 28 including a syringe plunger 30 and a needle 32. The bore in the syringe carrier 24 may be designed to be an interference fit at its forward end with a part of the syringe so as lightly to grip the syringe. The syringe carrier 24 is provided at its forward end with a rib (not shown) that limits rearward movement of the syringe carrier under the influence of the spring 26.

The rearward housing part 12 contains a constant force drive spring 34 wrapped around a drum 36. The outer end of the constant force spring is secured to an anchorage (not shown) on the inner part of the rearward housing part 12. The drum 36 is mounted for rotation in a drive piston 38 and the constant force spring is designed to be energised as the drive piston 38 is moved to its rearward position as shown in FIG. 1. The drive piston 38 may be latched in its cocked position and released by any suitable mechanism, but this is done in the present embodiment by means of a trigger 40 provided on the rearward housing part 12.

The drum 36 defines a recess 42 in which is confined a spherical magnet 44 having north and south poles. In the base of the recess 42 is provide a soft iron keeper element 46 which, in the absence of other magnetic influences, retains the spherical magnet against the base of the recess 42.

The rearward housing part 12 has provided in a wall thereof a captive, fixed, magnet 48 positioned at the forward end of the operational stroke of the drive piston 38. The captive magnet 48 is positioned such that magnetic attraction between the captive magnet and the moveable magnet 44 overcomes the attraction between the moveable magnet 44 and the keeper 46 when the drive piston has moved to a position in which the injection is complete. The resultant 'click' as the moveable magnet impacts the fixed magnet therefore gives an audible indication that the injection is complete. The impact will also generate a tactile signal that can be felt by the user.

In other embodiments, not shown, different types of audible, tactile or visual indicators may be provided. For example, co-acting magnets may be provided which cause an element to project or retract into the housing so that the user can feel for an indication of injection complete.

An important feature of the magnetically-operated indicator is that it does not divert energy from the main constant force spring that expels the dose. In fact energy is required during priming of the device to separate the magnets but this does not significantly diminish the energy available for expelling the dose.

An injection cycle will now be described. The forward and rearward housing parts are unscrewed and the drive piston 38 pushed back to the cocked position by reversing the forward housing part and pushing the piston back using the nose of the cap 18 until it is latched by the trigger. As the drum 36 moves rearwardly, the spherical magnet 44 is pulled away from the captive magnet 48 and is pulled back towards the keeper 46 by magnetic attraction.

A syringe is then loaded into the syringe carrier 24 in the forward housing part 10 and the housing parts screwed together. The cap is removed during or after this operation by suitable means (such as is described below). The auto-injector is then in the condition shown in FIG. 1 ready to be fired. On firing, the drum 36 and drive portion 38 are released for forward movement under the influence of the drive spring 26 so that the drive piston 38 moves the syringe plunger 30 forward to expel the dose. Towards the end of the stroke, when the required amount of the drug has been expelled, the drum 36 is close enough to the captive magnet for the captive magnet to attract the spherical magnet with a force greater than that exerted by the keeper so that there is a loud click indicating injection complete.

Figure 6:
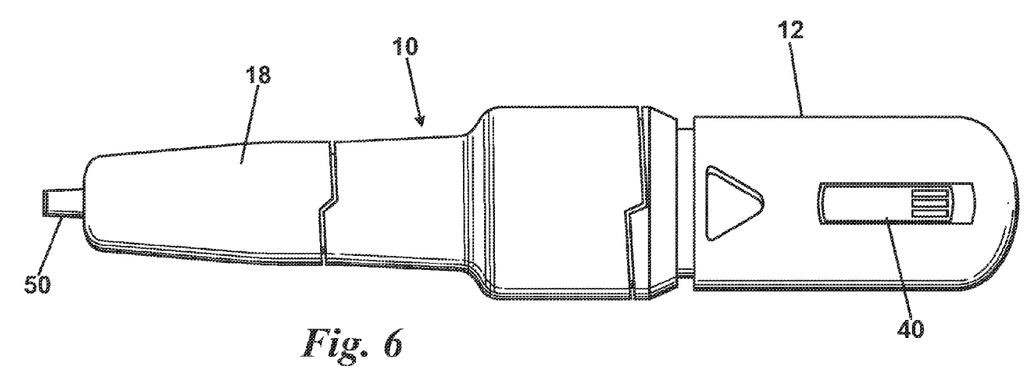
FIG. 6 is a longitudinal view with the syringe loaded and the needle sheath projecting a short distance from the front end of the housing.
Figure 7:
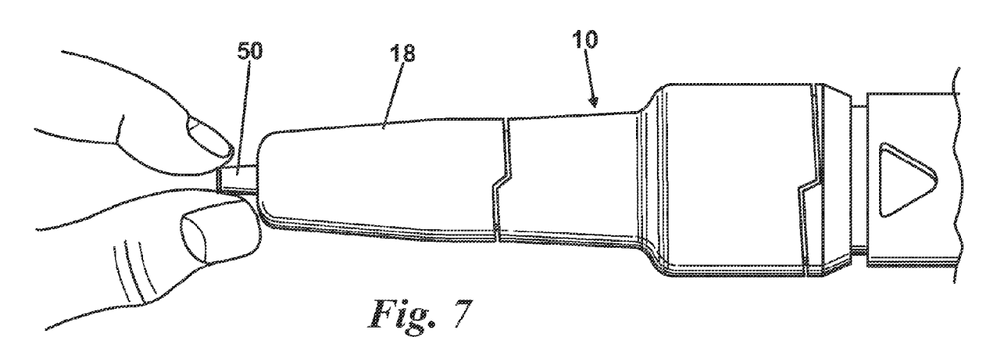
FIG. 7 illustrates the difficulty of securely gripping the needle sheath for removal.
Figure 8:
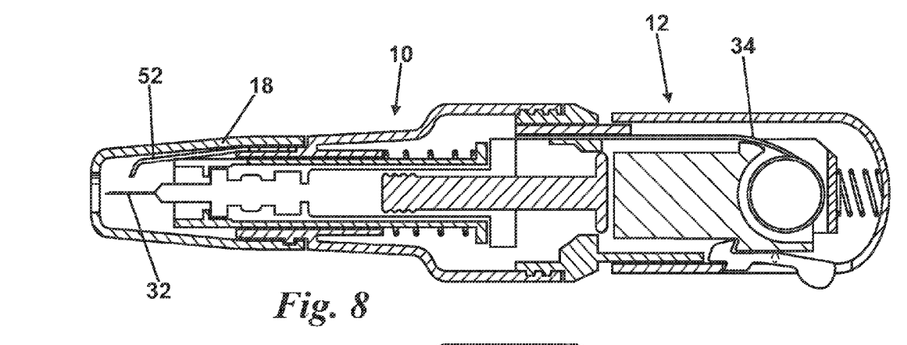
FIG. 8 is a longitudinal cross-sectional view through a second embodiment of auto-injector adapted to facilitate removal of the needle sheath.
Figures 9, 10, 11:
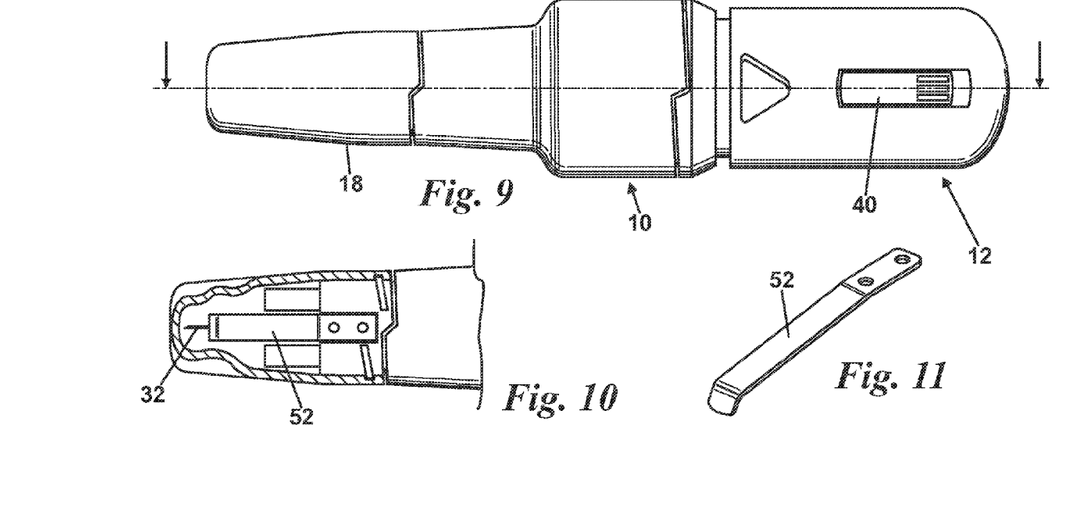
FIG. 9 is a longitudinal view of the second embodiment of auto-injector.
FIG. 10 is a part-sectioned, detailed view on the front end of the housing showing the spring finger incorporated in the embodiment of FIGS. 8 and 9.
FIG. 11 is a perspective view of the spring finger.
Figure 12:
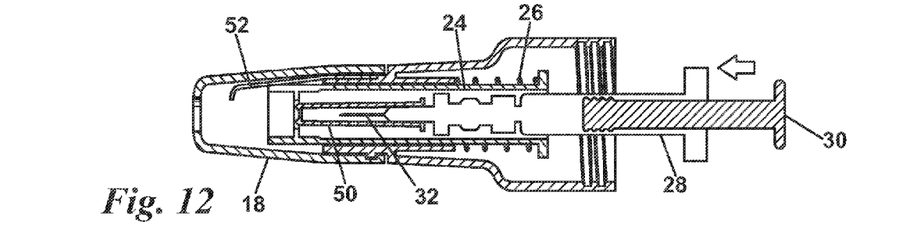
FIGS. 12 and 13 are successive views showing insertion of a syringe with sheath into the front end of the housing with the spring finger latching behind the sheath.

Referring now to FIGS. 6 to 16, there is now described an arrangement for facilitating removal of the needle sheath. As seen in FIGS. 6 and 7, when assembled with the syringe in place prior to injection, a typical needle sheath 50 extends only a short way forward of the cap 18. This is not enough to enable someone to grip the needle sheath sufficiently tightly to remove it. There is a risk therefore that the user circumvents this problem by removing the sheath 50 before inserting the syringe into the syringe carrier, with the attendant risk of needle-stick injury.

Figure 13:
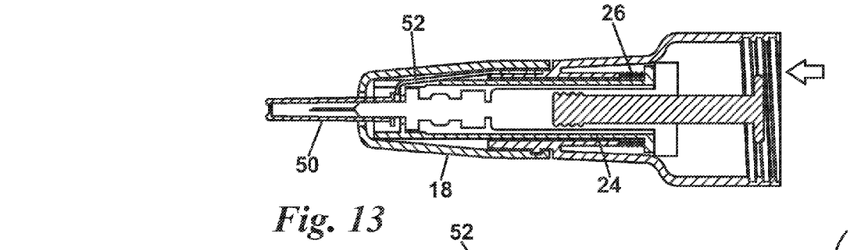
Figure 14:
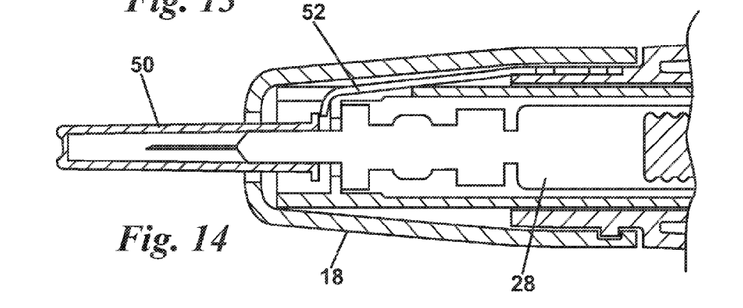
FIG. 14 is an enlarged detailed view on the front end of FIG. 13.
Figure 15:
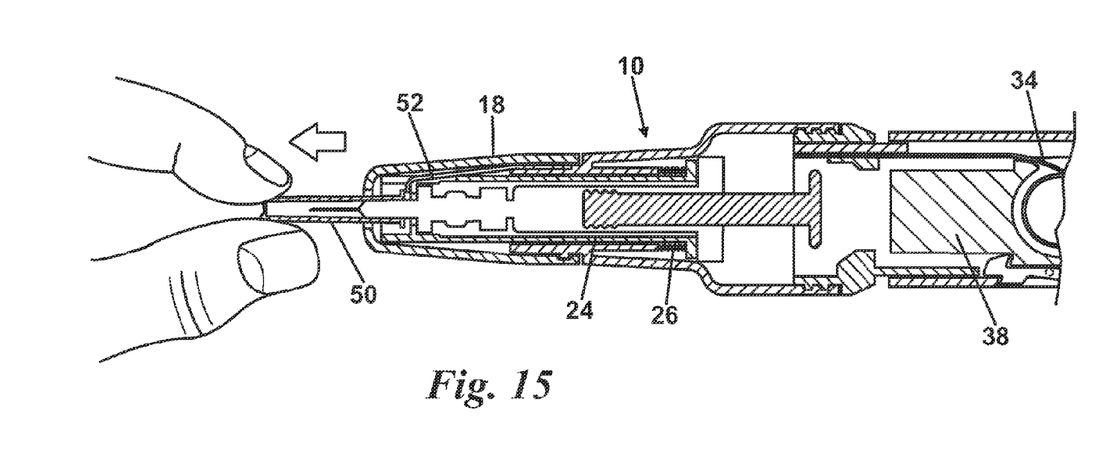
FIGS. 15 and 16 show successive steps in removal of the needle sheath and subsequent rearward movement of the needle and syringe.
Figure 16:
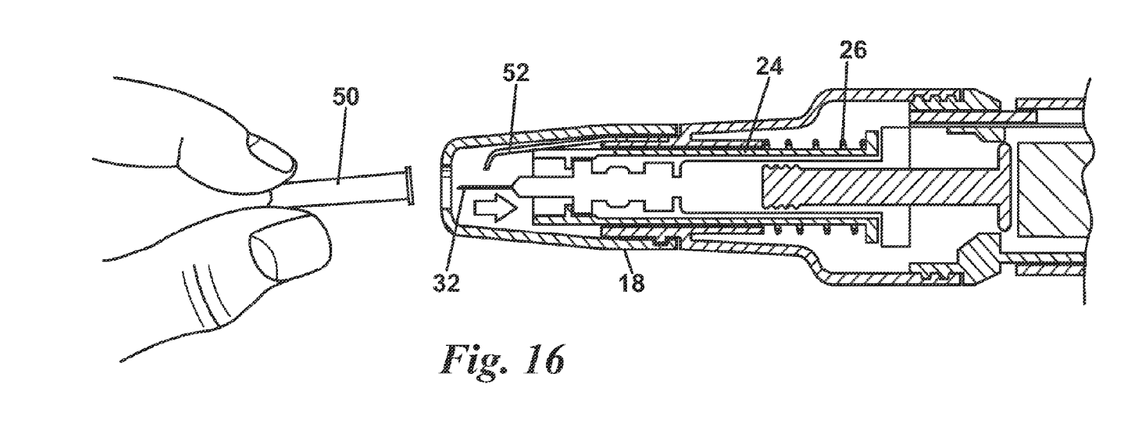

Accordingly, as seen in FIGS. 8 to 16, a spring finger 52 is provided that is anchored to the forward housing part or a component affixed thereto and extends forwardly and inwardly. The spring finger 52 is designed so that its forward end can latch behind the rearward annular rib of the needle sheath 50 when the syringe has been inserted into the syringe carrier 24 and the syringe carrier pushed forwardly against the bias of the spring 26 as seen in FIG. 13. The spring finger retains the syringe and sheath in this forward position leaving a much greater portion of the sheath available to be gripped and removed. As soon as the sheath is removed by easing it off, and thus overcoming the friction fit between the needle sheath and the needle hub of the syringe, the syringe shoots back rearwardly under the influence of the spring 26 so that the needle is safely within the cap 18. The device is then ready for use as previously described.

The invention claimed is:

1. An injection device, comprising:
   a syringe disposed within a housing;
   a drive element moveable from a first position to a second position to expel a dose from said syringe; and
   a magnetically-operated indicator for indicating an injection is complete,
   said magnetically-operated indicator including two co-acting elements, a first of said two co-acting elements being associated with said drive element, and a second of said two co-acting elements being associated with said housing, said first and second co-acting elements arranged such that, as said drive element arrives at or near said second position, a relative position of said first and second co-acting elements is changed by an influence of a magnetic force acting therebetween,
   wherein said second of said co-acting elements comprises a captive element and the first of said co-acting elements comprises a moveable element, and
   wherein a ferro-magnetic keeper element is associated with said drive element and configured to temporarily restrain said moveable element until said moveable element is moved under the influence of said magnetic force due to a proximity of said captive element.

2. An injection device according to claim 1, wherein said magnetically-operated indicator generates an audible indication that indicates the injection is complete.

3. An injection device according to claim 1, wherein said magnetically-operated indicator generates a visual indication that indicates the injection is complete.

4. An injection device according to claim 1, wherein said magnetically-operated indicator generates a tactile indication that indicates the injection is complete.

5. The injection device according to claim 1, wherein said drive element has associated therewith a recess for receiving said moveable element and permits transverse movement of said moveable element due to magnetic interaction of said moveable element with said captive element.

6. The injection device according to claim 5, wherein said recess extends transversely, and said ferro-magnetic keeper element is disposed at a first end region of said recess, said first end region being remote from an opposite second end region of said recess that faces said captive element when the drive element is at or near said second position.

7. An injection device according to claim 5, wherein said magnetically-operated indicator generates an audible indication that indicates the injection is complete.

8. The injection device according to claim 1, wherein said captive element is associated with said housing, and said moveable element is associated with said drive element.

9. The injection device according to claim 1, wherein both of said first and second co-acting elements are magnetized.

10. The injection device according to claim 5, wherein said magnetically-operated indicator generates a visual indication that indicates the injection is complete.

11. The injection device according to claim 5, wherein said magnetically-operated indicator generates a tactile indication that indicates the injection is complete.

12. The injection device according to claim 5, wherein said captive element is associated with said housing and said moveable element is associated with said drive element.

13. An injection device comprising:
    a syringe disposed within a housing;
    a drive element moveable from a first position to a second position to expel a dose from said syringe; and
    a magnetically-operated indicator for indicating an injection is complete,
    said magnetically-operated indicator including two co-acting elements, a first of said two co-acting elements being associated with said drive element, and a second of said two co-acting elements being associated with said housing, said first and second co-acting elements arranged such that, as said drive element arrives at or near said second position, a relative position of said first and second co-acting elements is changed by an influence of a magnetic force acting therebetween,
    wherein one of said first or said second of said co-acting elements comprises a captive element, and the other of said first or said second of said co-acting elements comprises a moveable element, and
    wherein said magnetically-operated indicator generates an audible indication that indicates injection is complete, said audible indication being produced as a result of an impact between said moveable element and either of said captive element or a surface associated therewith.

14. The injection device according to claim 13, wherein said impact also generates a tactile indication that indicates the injection is complete.

15. An injection device, comprising:
    a syringe disposed within a housing;
    a drive element moveable from a first position to a second position to expel a dose from said syringe; and
    a magnetically-operated indicator for indicating an injection is complete,
    said magnetically-operated indicator including two co-acting elements, a first of said two co-acting elements being associated with said drive element, and a second of said two co-acting elements being associated with said housing, said first and second co-acting elements arranged such that, as said drive element arrives at or near said second position, a relative position of said first and second co-acting elements is changed by an influence of a magnetic force acting therebetween,
    wherein one of said first or said second of said co-acting elements comprises a captive element, and the other of said first or said second of said co-acting elements comprises a moveable element,
    wherein both of said co-acting elements are magnetized, and
    wherein said drive element has associated therewith a recess for receiving said moveable element and permits transverse movement of said moveable element due to magnetic interaction of said moveable element with said captive element.

16. The injection device according to claim 15, wherein said captive element is associated with said housing, and said moveable element is associated with said drive element.

17. The injection device according to claim 15, wherein said magnetically-operated indicator generates an audible indication that indicates the injection is complete.

18. The injection device according to claim 15, wherein said magnetically-operated indicator generates a visual indication that indicates the injection is complete.

19. The injection device according to claim 15, wherein said magnetically-operated indicator generates a tactile indication that indicates the injection is complete.

\* \* \* \* \*